(12) United States Patent
Bron et al.

(10) Patent No.: US 12,175,649 B2
(45) Date of Patent: Dec. 24, 2024

(54) CHARACTERIZATION AND CLASSIFICATION OF SPOT WELDS BY ULTRASONIC DIAGNOSTIC TECHNIQUES

(71) Applicant: SCANMASTER SYSTEMS (IRT) LTD., Kfar Saba (IL)

(72) Inventors: Michael Bron, Kfar Saba (IL); Marina Uzelevski, Kfar Sava (IL); Tal Afek, Ramat Gan (IL)

(73) Assignee: SCANMASTER (IRT) LTD., Kfar Saba (IL)

( * ) Notice: Subject to any disclaimer, the term of this patent is extended or adjusted under 35 U.S.C. 154(b) by 703 days.

(21) Appl. No.: 17/050,489

(22) PCT Filed: Feb. 10, 2019

(86) PCT No.: PCT/IL2019/050162
§ 371 (c)(1),
(2) Date: Oct. 26, 2020

(87) PCT Pub. No.: WO2019/207562
PCT Pub. Date: Oct. 31, 2019

(65) Prior Publication Data
US 2021/0312604 A1    Oct. 7, 2021

Related U.S. Application Data

(60) Provisional application No. 62/662,836, filed on Apr. 26, 2018.

(51) Int. Cl.
*G01N 29/06*      (2006.01)
*G01N 29/11*      (2006.01)
(Continued)

(52) U.S. Cl.
CPC ....... *G06T 7/0004* (2013.01); *G01N 29/0645* (2013.01); *G01N 29/11* (2013.01);
(Continued)

(58) Field of Classification Search
CPC ................ G06T 7/0004; G06T 11/001; G06T 2207/10132; G06T 2207/30152;
(Continued)

(56) References Cited

U.S. PATENT DOCUMENTS 6,546,803 B1   4/2003   Ptchelintsev et al.
6,925,882 B1   8/2005   Fleming et al.
(Continued)

FOREIGN PATENT DOCUMENTS

| | | |
|---|---|---|
| CN | 106370733 A | 2/2017 |
| JP | 2008224226 A | 9/2008 |
| JP | 2017015668 A | 1/2017 |

OTHER PUBLICATIONS

Jenis, Walter. *Effect of welding nugget diameter on the tensile strength of the resistance spot welding joints of same sheets metal.* Diss. UMP, 2009.
(Continued)

*Primary Examiner* — Jonathan M Hansen
(74) *Attorney, Agent, or Firm* — The Roy Gross Law Firm, LLC; Roy Gross (57) ABSTRACT

A system for ultrasonic examination of spot welds comprising a probe, a computer, and a display screen, the computer configured for spot weld analysis by appropriate analytical software, the probe for coupling to a spot weld via a couplant, wherein the probe comprises a two dimensional array of sensors that is each configured to conduct an A scan analysis, thereby providing a color pixel indicating weld quality in terms of parameters selected from the group of size, shape, voids, upper sheet-weld nugget interface strength and lower sheet-weld nugget interface strength, such that the two dimensional array of sensors produces a two dimensional pixilated image indicating the weld quality in terms of selected parameters.

6 Claims, 6 Drawing Sheets

(51) Int. Cl.
  *G01N 29/12* (2006.01)
  *G01N 29/26* (2006.01)
  *G01N 29/44* (2006.01)
  *G01N 33/2045* (2019.01)
  *G01N 33/207* (2019.01)
  *G06T 7/00* (2017.01)
  *G06T 11/00* (2006.01)

(52) U.S. Cl.
  CPC .......... *G01N 29/12* (2013.01); *G01N 29/262* (2013.01); *G01N 29/4445* (2013.01); *G01N 33/2045* (2019.01); *G01N 33/207* (2019.01); *G06T 11/001* (2013.01); *G01N 2291/014* (2013.01); *G01N 2291/015* (2013.01); *G01N 2291/0289* (2013.01); *G01N 2291/106* (2013.01); *G01N 2291/2672* (2013.01); *G06T 2207/10132* (2013.01); *G06T 2207/30152* (2013.01)

(58) Field of Classification Search
  CPC .... G01N 29/0645; G01N 29/11; G01N 29/12; G01N 29/26; G01N 29/4445; G01N 33/2045; G01N 33/207; G01N 2291/014; G01N 2291/015; G01N 2291/0289; G01N 2291/10; G01N 2291/2672; G01N 2291/044; G01N 29/223; G01N 29/043; G01N 29/4436
  See application file for complete search history.

(56) References Cited

U.S. PATENT DOCUMENTS

| | | | |
|---|---|---|---|
| 6,948,369 | B2 | 9/2005 | Fleming et al. |
| 7,132,617 | B2 | 11/2006 | Lee et al. |
| 7,789,286 | B2 | 9/2010 | Maev et al. |
| 9,733,219 | B2 | 8/2017 | Spencer et al. |
| 2012/0310551 | A1* | 12/2012 | Na ...................... G01N 29/24 702/39 |
| 2015/0253288 | A1* | 9/2015 | Spencer ................ G01N 29/11 73/602 |

OTHER PUBLICATIONS

International Search Report of Application No. PCT/IL2019/050162 mailed on Apr. 30, 2019.
Waldo Perez-Regalado, "Ultrasonic Real-Time Quality Monitoring Of Aluminum Spot Weld Process Source", A Dissertation Submitted to the Faculty of Graduate Studies through Electrical and Computer Engineering in Partial Fulfillment of the Requirements for the Degree of Doctor of Philosophy at the University of Windsor, Oct. 22, 2013.
Waldo J Perez Regalado, et. al., "Integration of the Ultrasonic Real-Time Spot Weld Monitoring System Source", 5th Pan American Conference for NDT, Oct. 6, 2011.
Denisov AA, Shakarji CM, Lawford BB, Maev RG, Paille JM. Spot Weld Analysis With 2D Ultrasonic Arrays. J Res Natl Inst Stand Technol. Apr. 1, 2004;109(2):233-44. doi: 10.6028/jres.109.015. PMID: 27366607; PMCID: PMC4853110.
Jenis, W. (2009). Effect of Welding Nugget Diameter On the Tensile Strength of the Resistance Spot Welding Joints of Same Sheets Metal [PhD Dissertation]. University Malaysia Pahang. Available online: [https://core.ac.uk/download/pdf/159176951.pdf].
Regalado, W.P., Chertov, A.M., Maev, R.G., & Furlanetto, V. (2011). Integration of the Ultrasonic Real-Time Spot Weld Monitoring System. 5th Pan American Conference for NDT. Available online: [https://www.ndt.net/article/panndt2011/papers/124_Perez%20Regalado.pdf].
Perez Regalado, W. J., "Ultrasonic Real-Time Quality Monitoring Of Aluminum Spot Weld Process" (2014). Electronic Theses and Dissertations. 5020. https://scholar.uwindsor.ca/etd/5020.
PCT International Search Report for International Application No. PCT/IL2019/050162, mailed Apr. 30, 2019, 5pp.
PCT Written Opinion for International Application No. PCT/IL2019/050162, mailed Apr. 30, 2019, 4pp.
PCT International Preliminary Report on Patentability for International Application No. PCT/IL2019/050162, issued Aug. 19, 2020, 15pp.

\* cited by examiner

| Coupon #, Point # | Controlled Spot | Phased Array VP's Representation | Automatic Algorithm Classification | Element Distribution Statistics* |
|---|---|---|---|---|
| 1, A | Good nugget |  | Good | Green =>30<br>Blue<30<br>Orange=<40<br>Red<5 |
| 2, D | Undersize spot / small nugget |  | Undersize | Green=>20<br>Green=<29<br>Blue=>31<br>Blue=<40<br>Orange>20<br>Red<5 |
| 2, E | Stick weld / discrepant |  | Discrepant | Green=<20<br>Blue>45<br>Orange>22 |
| 1, B | Cold nugget / no weld |  | No weld | Green<5<br>Blue=>80 |
| 2, F | Thin weld / strong indentation |  | Thin Spot | Green=<10<br>Blue=>15<br>Orange=>55 |

Table 5: Phased Array Element Representation

* Element count

Fig. 17

CHARACTERIZATION AND CLASSIFICATION OF SPOT WELDS BY ULTRASONIC DIAGNOSTIC TECHNIQUES

CROSS-REFERENCE TO RELATED APPLICATIONS

This application is a National Phase Application of PCT International Application No. PCT/IL2019/050162, International Fling Date Feb. 10, 2019, claiming the benefit of U.S. Patent Application No. 62/662,836, filed Apr. 26, 2018, which are hereby incorporated by reference.

BACKGROUND

Resistance spot welding is a process in which contacting metal surface points are joined together using the heat obtained from resistance to electric current. It is a subset of electric resistance welding.

Work-pieces are held together under pressure exerted by electrodes. The technique is typically used for welding sheets of metal together, and these sheets are usually in the 0.5 to 3 mm (0.020 to 0.118 in) thickness range. The spot welding process uses two shaped copper alloy electrodes to concentrate the welding current into a small "spot" and to simultaneously clamp the sheets together. Forcing a large current through the spot melts the metal and forms the weld. Spot welding is an attractive joining technique since a lot of energy can be delivered to the spot in a very short time (approximately 10-100 milliseconds), which permits the welding to occur without excessive heating of the rest of the work-pieces and high quality welds can be achieved at low cost. Consequently, spot welding has become very widely used in the automobile industry where it is used almost universally to weld pieces of sheet metal together to form the body of cars. The average car contains several thousand spot welds that are essential to its structural integrity. The spot welding process may be completely automated, and many of the industrial robots found on assembly lines are spot welders.

The amount of heat (energy) delivered to the spot is determined by the resistance between the electrodes and the magnitude and duration that the welding current is applied. The amount of energy is chosen to match the sheet's material properties, its thickness, and the type of electrodes. The energy delivered to the spot can be accurately controlled to produce reliable welds. Applying too little energy will not melt the metal or will make a poor weld. Applying too much energy will melt too much metal, eject molten material, and may make a hole rather than a weld.

Spot welding is typically used to weld together sheet metal, welded wire mesh and wire mesh. Thicker stock is more difficult to spot weld because the heat flows into the surrounding metal more easily making it difficult to locally achieve the temperatures required to melt and fuse the contacting metal.

Although most often used to weld steel, aluminium alloys can also be spot welded, but because of their much higher thermal conductivity and electrical conductivity, higher welding currents are required, which in turn requires using larger, more powerful, and more expensive welding transformers.

The melted and resolidified material of the spot weld is sometimes referred to as a 'nugget'. The spot weld nugget is anisotropic and has a microstructure that is very different from that of the base metal.

The strength of a weld depends on various parameters including the size of the nugget, the area of the nugget in contact with each sheet and the strength of the contact. If molten metal is ejected, the nugget may contain voids.

In manufacturing, welds are used to join two or more metal surfaces. Because welds may encounter high load and cyclic loading leading to fatigue during the product lifetime, there is a chance that welds may fail if not created to the proper specification.

It will be appreciated that the spot weld joining two sheets together is typically hidden by the sheets themselves, so visual inspection is not possible. Testing of weld strength may be destructive or non-destructive.

Destructive testing includes macro etch testing, fillet-weld break tests, transverse tension tests, and guided bend tests. It will be appreciated that random sampling by destructive testing for quality control purposes is expensive as the parts tested are then scrapped.

To stay competitive, the automotive industry requires a spot weld inspection solution that facilitates increased production volumes while maintaining the highest quality standards.

Weld quality assurance widely uses Non Destructive Testing (NDT) technological methods and actions to test or assure the quality of welds, and secondarily to confirm the presence, location and coverage of welds. There, are various types of non-destructive testing. Most simply, Acoustic emission methods monitor load or flex the weld and monitor for the sound generated thereby. A weld can also be tapped and the sound made will indicate problems to the trained ear.

More sophisticated non-destructive methods include fluorescent penetrate tests, magnaflux tests, eddy current (electromagnetic) tests, hydrostatic testing, tests using magnetic particles, X-rays and gamma ray based methods and acoustic emission techniques.

Of the various Non Destructive Testing (NDT) techniques available, thermal/infrared, electrical conductivity, x-ray and eddy-current techniques have been shown to fail to reliably detect certain types of defective welds. Amongst the NDT methods, the ultrasonic (UT) method is considered the most efficient and the most reliable. For automated non-destructive testing with of weld spots, ultrasonic testing is widely used.

The study of acoustic wave propagation in the weld nugget includes metallurgical analysis and characterization of the mechanical and physical properties of weld nuggets, including dendrite structures and ferrous areas. Further, the propagation and the interaction of focused acoustic beams inside the spot weld may be analyzed. From this analysis and characterization, the connection between weld nugget structures and the associated acoustic images may be understood.

Ultrasonic testing uses the principle that a gap or inclusions of a different material within the weld changes the propagation of ultrasonic sound through the metal. One common method uses single-probe ultrasonic testing involving either operator interpretation of an oscilloscope-type screen, or by special algorithms to analyze the so-called A scan. Other methods use a matrix, or phased array of ultrasonic sensors.

In conventional ultrasonic testing an ultrasonic probe with a single crystal sends a high pitched mechanical vibration into the work-piece over the spot weld and signals reflected back are analized to indicate the quality of the weld.

In phased array ultrasonic testing virtual ultrasonic probes sequentially send a high pitched mechanical vibration into the work-piece over the spot weld and the reflected signals detected indicate the size of the weld.

The benefits of ultrasonic testing include direct cost savings and indirect savings. Direct cost savings include reduced inventory loss, reduced inspection time and improved testing safety. There are also indirect cost savings including the improved reliability of welds and improved reliability of welding process. Since ultrasonic testing technique a may be highly automated, each weld can be fully documented.

The most common acoustic examination methods are known as A, B and C Scans. The A scan is the most simple and widely used. It consists of showing the amplitude of ultrasound signal reflections (echoes) as a function of time at a selected point on the surface of the workpiece.

The B scan uses the same procedure as the A scan, but the probe is moved in a line over the surface of the workpiece, and provides a section scan rather than point data, as an image through the sample is built up. The measured amplitude is shown as a dot on XY coordinates where X indicates position and Y indicates traveling time of the echo (depth).

By scanning at different depths, a C scan may be obtained, but this is time consuming.

The first PC based spot welding inspection systems were developed in the mid 1990s. Although a single crystal was used, the analysis of the weld quality was performed by analyzing one or more A-scans by the operator or by dedicated algorithms. A reasonable correlation between ultrasound generated parameters and examination of the weld by destructive methods was obtained. However, single crystal systems were not able to provide an indication of the nugget size, which is a critical characteristic of the weld.

In the early part of the $21^{st}$ century, systems using a two-dimensional array of sensors were introduced. These enable the mapping of the size and shape of the nugget. For fast evaluation purposes, circles are usually drawn within and around the nugget, and if there is sufficient material within the inner circle, and the outer circle is not too large, the weld is considered acceptable.

It will be noted, however, that the actual strength of a weld is determined by the true contact area between the nugget and the upper and lower work-pieces that are welded together, and by the strength of the weld interface. If the weld is elongated, it may not map well with inner and outer circles, but could nevertheless, be strong enough, and scrapping acceptable welds is expensive and wasteful. Sometimes, a nugget appears to be adequate in side, but due to air bubbles and similar inclusions, the strength of the weld may be inadequate.

The present invention provides methods for more accurate ultrasonic testing and diagnosis of weld quality.

U.S. Pat. No. 7,132,617 to Hsu-Tung lee et al. titled "Method and System for Assessing the Quality of Spot Welds" characterizes spot welds in terms of their size, calculating large and small diameters. The patent specification describes a system and method for assessing the quality of spot weld joints between pieces of metal. The system includes an ultrasound transducer probing a spot weld joint. The ultrasound transducer transmits ultrasonic radiation into the spot weld joint, receives corresponding echoes, and transforms the echoes into electrical signals. An image reconstructor connected to the ultrasound transducer transforms the electrical signals into numerical data representing an ultrasound image. A neural network connected to the image reconstructor analyzes the numerical data and an output system presents information representing the quality of the spot weld joint. The system is trained to assess the quality of spot weld joints by scanning a spot weld joint with an ultrasound transducer to produce the data set representing the joint; then physically deconstructing the joint to assess the joint quality.

U.S. Pat. No. 7,789,286 to Maev et al titled "Method and apparatus for assessing the quality of spot welds" describes a method and apparatus for evaluating the size and/or quality of a spot weld. The apparatus includes a two-dimensional array of ultrasonic transducers arranged with a delay line for positioning adjacent a surface of a weld. A layer of gel is placed between the delay line and the weld surface. The array of transducers emit ultrasonic waves that are directed into the weld and are partially reflected by the various interfaces. The reflected waves are received by the transducers and relayed to a central processing unit that analyzes the time delay, amplitude, and amplitude attenuation to calculate the border of the weld nugget, the thickness of the welded material, the thickness of the gel layer, and other factors contributing to weld quality.

SUMMARY OF THE INVENTION

A first aspect of the invention is directed to a system for ultrasonic examination of spot welds comprising a probe, a computer, and a display screen, the computer configured for spot weld analysis by appropriate analytical software, the probe for coupling to a spot weld via a couplant, wherein the probe comprises a two dimensional array of sensors that is each configured to conduct an A scan analysis, thereby providing a color pixel indicating weld quality in terms of parameters selected from the group of size, shape, voids, upper sheet-weld nugget interface strength and lower sheet-weld nugget interface strength, such that the two dimensional array of sensors produces a two dimensional pixilated image indicating the weld quality in terms of selected parameters.

In some embodiments, the number of rows and columns in the pixilated image is less than the number of rows and columns of ultrasonic sensors in the probe.

In some embodiments, individual parameters may be isolated and threshold values set for one or more parameters, enabling a weld to be accepted by an algorithm based on there being more than a threshold number of acceptable weld pixels of a particular category or rejected by the algorithm determining there being less than a threshold number of acceptable weld pixels of a particular category.

A second aspect of the invention is directed to providing a method for the ultrasonic examination of spot welds comprising the steps of providing the system a system for ultrasonic examination of spot welds comprising a probe, a computer, and a display screen, the computer configured for spot weld analysis by appropriate analytical software, the probe for coupling to a spot weld via a couplant, wherein the probe comprises a two dimensional array of sensors that is each configured to conduct an A scan analysis, thereby providing a color pixel indicating weld quality in terms of parameters selected from the group of size, shape, voids, upper sheet-weld nugget interface strength and lower sheet-weld nugget interface strength, such that the two dimensional array of sensors produces a two dimensional pixilated image indicating the weld quality in terms of selected parameters;

generating an array of A scans;
    setting thresholds for various parameters, generating a colour mapping of a weld corresponding to values of key parameters, and
    characterizing the weld in terms of the number of pixels of each key parameter that passes the threshold.

In some embodiments, by isolating individual parameters and setting threshold values for each pixel, a decision may be made to accept or reject a weld.

In some embodiments, by isolating individual parameters and setting threshold values for acceptability of each part of the weld, the size of the weld may be calculated.

In some embodiments, by isolating individual parameters and setting threshold values for each pixel, an algorithm may be used to accept or reject the weld based on there being more than a threshold number of acceptable weld pixels of a particular category or rejected by the algorithm determining there being less than a threshold number of acceptable weld pixels of a particular category.

BRIEF DESCRIPTION OF THE FIGURES

For a better understanding of the invention and to show how it may be carried into effect, reference will now be made, purely by way of example, to the accompanying Figures, wherewith it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

In the drawings, like components are generally designated by like reference numerals, wherein:

FIG. 4 to 8 are metallographic longitudinal sections through spot welds between two sheets of metal, where

DESCRIPTION OF EMBODIMENTS

Figure 1:
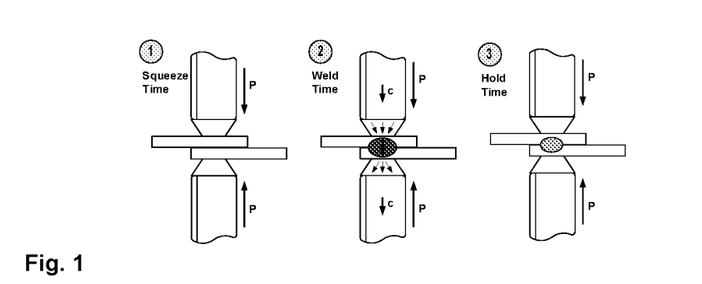
FIG. 1 shows the steps 1, 2 and 3 for spot welding two sheets together.

With reference to FIG. 1, welds are formed by applying local pressure to electrodes pressed against two sheets in contact, ensuring contact between two sheets (step 1) and then heat is applied (step 2), typically electrically, to locally melt and fuse the sheets to produce a nugget joining the two sheets step 3.

The weld thus formed is concealed between the two sheets of metal that are joined thereby and cannot be examined visually without destroying the work pieces.

The quality of the spot weld is affected by the welding processes and the design of the joint. Many factors affect the weld strength and quality, including metallurgic reactions, thermal behavior, chemical composition, the condition of the base metal, welding conditions, and the welding equipment used. The intricate relationships between these factors makes it difficult to control the quality of spot welds. The weld quality indicators related to by the various standards are mostly for visual inspection and for destructive testing which are typically separately conducted. Visual examination is superficial and the weld nugget itself is generally concealed by the sheets of metal it holds together, only allowing visual inspection of the weld site on the exposed surface. The true quality of the spot weld. i.e., its strength, can only be determined by off-line destructive sample tests. It can be used for random sampling statistics based quality control, but does not allow testing of the actual spot welds that are subsequently subjected to stress in use.

Acoustic methods are a commonly used non-destructive testing method that has been used for various inspection applications. The acoustic method provides both surface and internal information and has a high sensitivity to small discontinuities. Acoustic methods require a propagating medium or couplant fluid for acoustic wave propagation between the acoustic probe and the test specimen. Since the sheet metal components that are spot welded in the automotive and aerospace industries are usually galvanized or coated, they are not be damaged by the couplant fluid.

Unfortunately, skillful operators are required for operating acoustic testing devices and for analyzing the information generated by such systems. This makes on-line inspection of spot welds difficult because it is not economical to train large numbers of workers in ultrasonic testing.

Unlike optical or x-ray inspection methods that obtain two-dimensional information through one process, ultrasonic testing has to go through point-to-point scanning procedures to obtain information from the whole inspected volume. There are several ways to display acoustic information, and they can be categorized by the information obtained. The most common ones are A-, B-, and C-scans that can be selected to show the internal defects as required.

The A-Scan is the simplest and mostly widely used method of displaying information with conventional ultrasonic NDE devices. It shows the amplitude of the echoes, or the reflection, as a function of time at a selected point on the work surface. The duration of time between different peaks represents the time needed for acoustic waves to travel between discontinuities. It provides sample thickness information.

The B-scan follows the same procedure as the A-scan, but repeats the signal-catching procedures while the probe scans along a straight line on the surface of the work-piece being tested. Thus, an image of the cross-section of a component is built up. The measured amplitude is displayed as a colored dot on a monitor and its position is defined by the position of the probe (X-coordinate) and the traveling time (Y-coordinate) of the acoustic pulse. If the amplitude of a particular echo is monitored at each point on a certain depth of the workpiece, a C-scan can be performed. Measurements at each point are taken using two-dimensional scanning and electronic gate mechanisms that produce the plan for the level of the defect. This scan only gives the information at the preset depth of the electronic gate. While the C-scan provides the richest information, and is therefore more desirable for quality control purposes, it is also the most time consuming scan, and therefore difficult to perform on-line.

Conventional spot weld inspection used on production lines uses a probe with one ultrasonic element and analyzes A-scan data.

Figure 2:
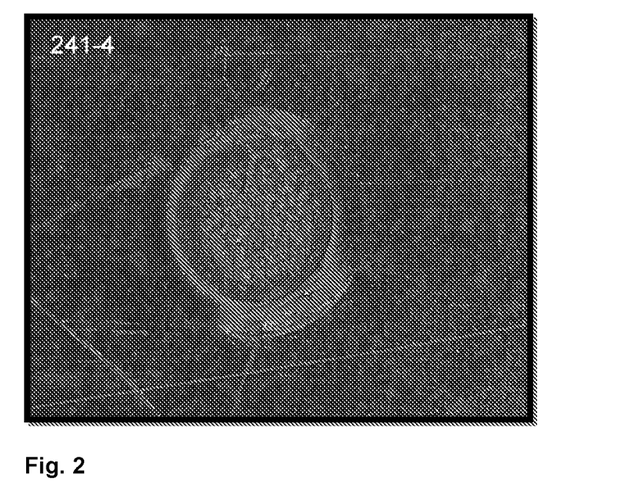
FIG. 2 is a planar photograph of a weld after destructive testing.

FIG. 2 is a photograph of such a weld, obtained by chiseling the two welded sheets apart. For testing coupons for optimizing weld conditions, this technique may be acceptable, but for on-going quality assurance, it is time consuming and often the separated parts have to be discarded and cannot be rewelded.

Although " . . . different diameter of nugget would shows different tensile strength" Walther Jenis (2009) 'Effect of welding nugget diameter on the tensile strength of the resistance spot welding joints of same sheets metal', University Malaysia Pahangs, it was pointed out by Dickenson D. "*Welding in the automotive industry*", Committee of Sheet Steel Producers, Report 81-5, AISI, (1981), that there is not always a correlation between weld diameter and weld strength.

Figure 3A:
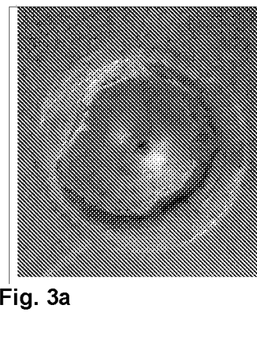
FIG. 3a-3c show real spot welds, showing how a weld may be non circular, such that an inner inscribed circle will ignore a significant percentage of the weld area, implying that the weld is too small, and an outer inscribed circle gives a stronger result than actually produced.
Figure 3B:
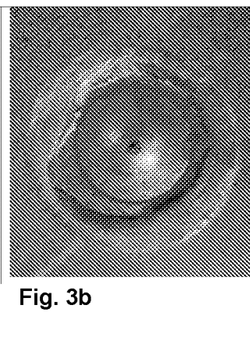
Figure 3C:
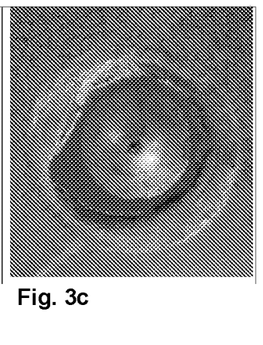

It will be appreciated that round nuggets are an idealization. Where the electrodes are worn, there is poor tip alignment or dirt on the workpieces, non-round spot welds may occur. FIG. 3 shows a real weld, and attempts to fit an inscribed circle underestimates the weld area by $\frac{1}{5}$ to $\frac{1}{3}$. This discrepancy between assumed circular nuggets and actual shape goes some way to explain the difference between the expected and accurate strength of spot welds.

FIG. 4 to 8 are metallographic longitudinal sections through spot welds between two sheets of metal, showing common types of weld that may be obtained in practice. On a manufacturing, line periodically two test pieces may be welded, or a work piece may be scrapped to obtain such longitudinal sections. This technique can only be used on test samples, and not to directly examine welds that can be passed as inspected. Sectioning also cannot be used to examine 3 layer structures, painted parts or high strength steel Destructive testing of this type is very costly. It is estimated to cost several hundred million dollars a year in the US through loss of value added inventory.

Figure 4:
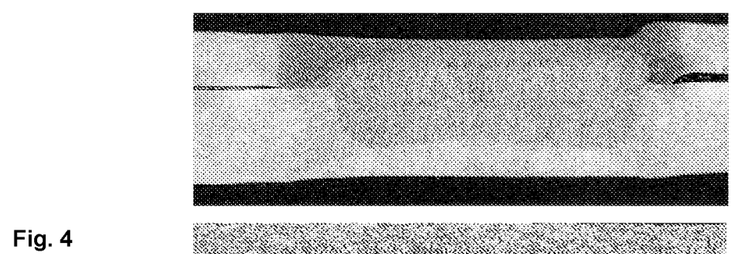
FIG. 4 is a metallographic longitudinal section through a quality weld nugget joining two sheets of metal.

FIG. 4 is a metallographic longitudinal section through a quality weld nugget 42 joining an upper sheet of metal 44 to a lower sheet of metal 46. This is the type of weld obtained where adequate pressure is applied to enable a high current to flow, melting the metal of each sheet 44, 46, and fusing them into a nugget 42.

Figure 5:
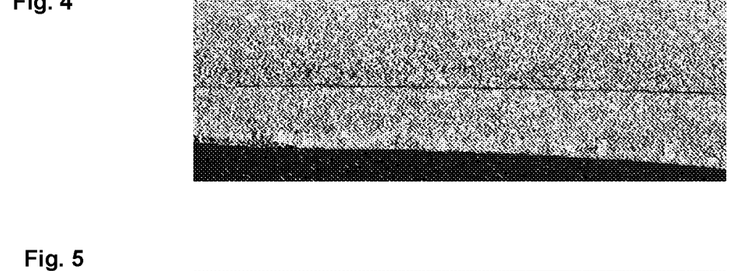
FIG. 5 is a metallographic longitudinal section of two adjacent sheets, where there is no weld so that there is nothing holding the two sheets in contact.

FIG. 5 is a metallographic longitudinal section of two adjacent sheets 54, 56, where there is no weld so that there is nothing holding the two sheets 54, 56 in contact. This could be the result of non contact pressure or no heat/electrical flow to melt and fuse the contacted surfaces of the two sheets 54, 56.

Figure 6:
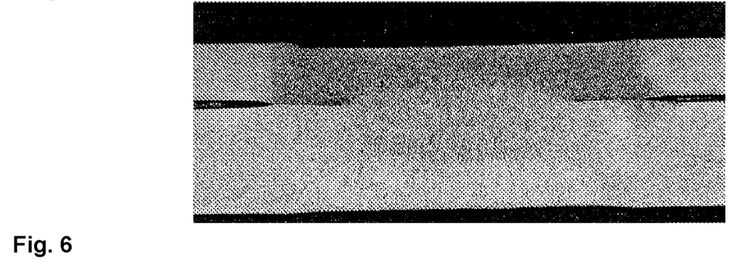
FIG. 6 is a metallographic longitudinal section of two adjacent sheet, weakly held together by an undersized weld.

FIG. 6 is a metallographic longitudinal section of two adjacent sheets 64, 66, weakly held together by an undersized weld 62. This could be the result of an adequate contact pressure but inadequate heat/electrical flow to melt and fuse a sufficient quantity of contacted surfaces of the two sheets 54, 56. Thus the material melts and a weld nugget 52 forms, but it is undersized, and may fail if subject to forces trying to separate the sheets 54, 56.

Figure 7:
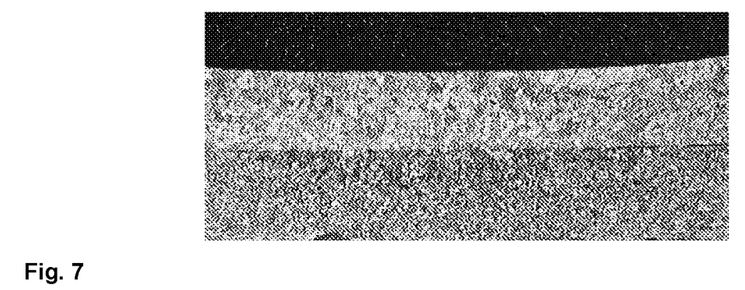
FIG. 7 is a metallographic longitudinal section of two adjacent sheets held together by cold welding, where the materials have fused together but there is no weld nugget, and such joins are typically very weak.

FIG. 7 is a metallographic longitudinal section of two adjacent sheets 64, 66 held together by cold welding, where the contacting surfaces 68 have fused together but there is no weld nugget. Such joins are typically very weak. They are formed by adequate pressure, but inadequate melting.

Figure 8:
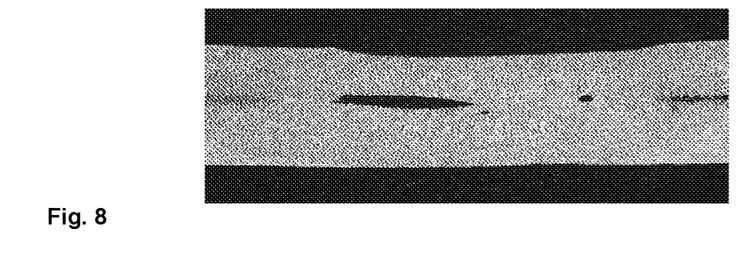
FIG. 8 is a metallographic longitudinal section of two adjacent sheets held together by a weld where there is a void in the center of the weld, so the weld is ring shaped.

FIG. 8 is a metallographic longitudinal section of two adjacent sheets 74, 76 held together by a weld 72 where there is a void 78 in the center of the weld 72, so the weld is ring shaped. This is a typical defect where other heating has caused bubbling. Such voids 78 are a potential source of weakness. Furthermore, if only the apparent size of the weld nugget 72 is measured, such voids 78 are not detected and the contact area and strength are assumed to be much higher than they are in practice.

The ultrasonic method for spot weld inspection is based on the detection of multiple reflections from the back wall of the welded structure, together with intermediate echoes reflected by the interface between the plates. The length of the echo sequence from the total thickness, the signal attenuation (amplitude drop), and the amplitude and position of the intermediate echoes permit the differentiation between good spot welds and defective ones, and enable a fuller classification of defective spots.

This enables, automated decision making, defect classification and reporting.

Figure 9:
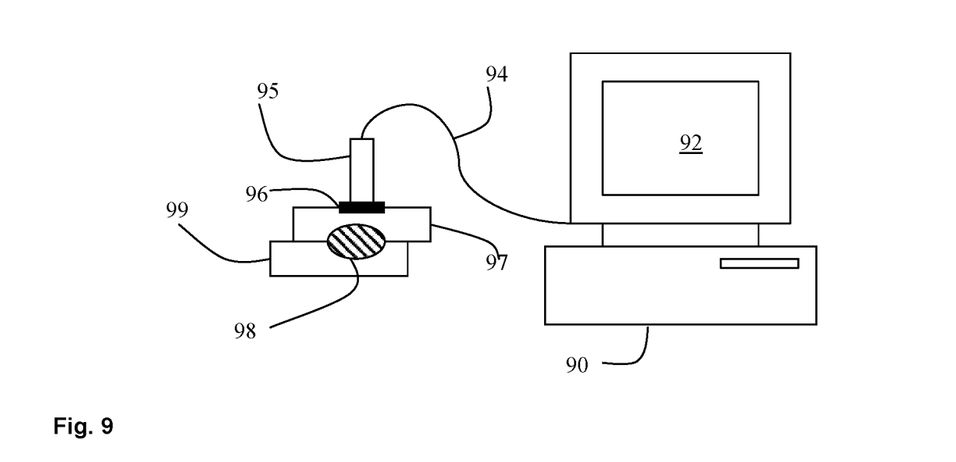
FIG. 9 is a schematic illustration of a system comprising a computer in data communication with a contact transducer coupled by a couplant to a work piece including a spot-weld.

With reference to FIG. 9, a schematic illustration of a testing system and a test-piece is shown. The testing system consists of a computer 90, such as a PC with a screen 92 for displaying visual information relating to ultrasonic signal attenuation, such as signal strength with distance, two dimensional representations of signal attenuation over a surface and the like. An ultrasonic probe 95 coupled to the computer by a wire 94 is coupled by a couplant 96 to a test-piece 99 consisting of an upper plate 97 coupled to a lower plate 99 by a spot weld 98.

It will be appreciated that weld machines often depress the metal sheets on one or both sides of the spot welds, giving irregular curved surfaces. The transmission and reflection coefficients of an ultrasound signal are sensitive to the tilt of the surface. Thus the signal attenuation is affected by the curvature of the indentation and not just by attenuation within the nugget.

Figure 10:
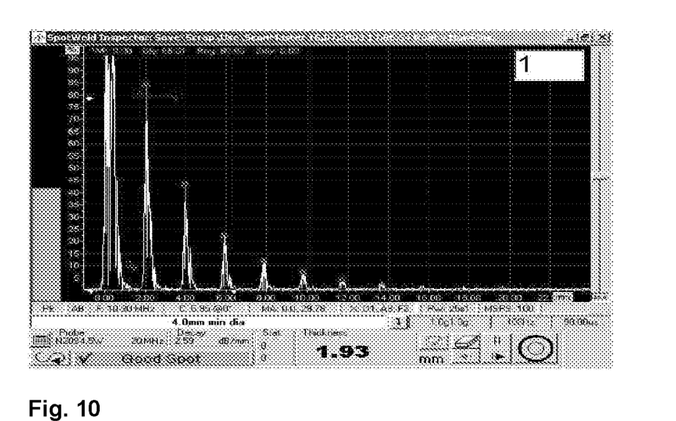
FIG. 10 is an A scan signal of the weld of FIG. 4.

With reference to FIG. 10, an A scan signal of the weld of FIG. 4 is shown showing an intensity of reflected signal vs. distance chart, characterized by well resolved peaks with no intermediate signals. This enables the total thickness of the weld (thickness of the upper sheet 97, the lower sheet 99 and the thickness of the weld nugget 98) is 1.93 mm. The decision making may be automated, so that such a weld is classified as good. Essentially, in a good weld, the energy propagates evenly. However, the weld attenuates the signal more than the sheet metal itself.

Figure 11:
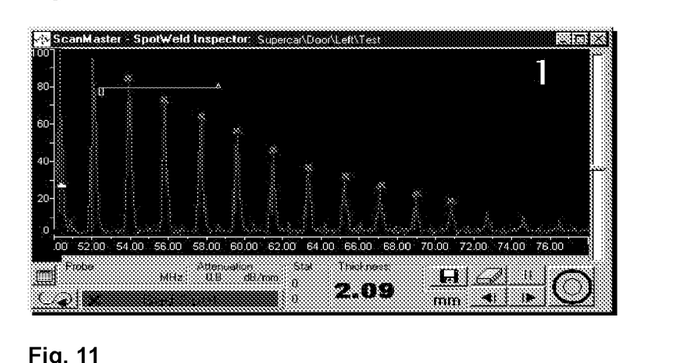
FIG. 11 is an A scan signal generated by the no weld shown in FIG. 5.

With reference to FIG. 11, an A scan signal generated by the no weld shown in FIG. 5 is reproduced. The most obvious detail of no weld is the repeat echo separation equivalent to the top plate thickness. The attenuation of the top plate 97 backwall echo is a characteristic of the grain structure of the plate material remaining unmodified due to lack of a nugget 98 and its melted structure. As shown in FIG. 11, the back wall signals are spaced at the top sheet thickness (T1).

Figure 12:
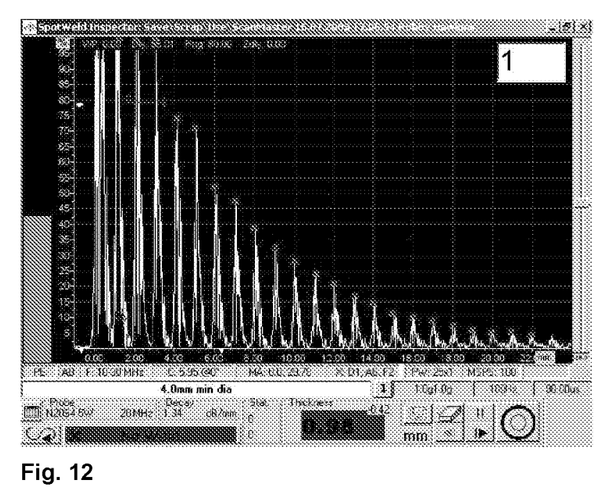
FIG. 12 is an A scan signal wherein the back wall signals are spaced at the top sheet thickness (T1).

With reference to FIG. 12, an A scan signal representing an undersized spot weld, such as that of FIG. 6 is shown.

Since the probe response is determined by the nugget diameter, undersized weld nuggets are characterized by their top plate signal echoes. The envelope of the intermediate echoes exhibits a maximal value that allows the differentiation of a small spot weld from a stick weld or a porous weld discussed below.

Figure 13:
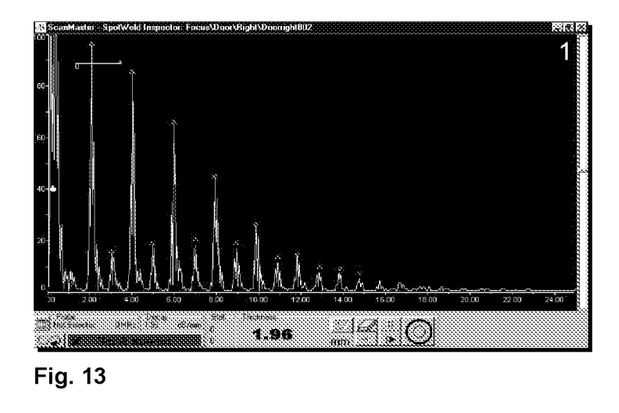
FIG. 13 is an A scan signal representing an undersized spot weld, such as that of FIG. 6 is shown.

With reference to FIG. 13, an A scan signal representing a stick spot weld is shown, corresponding to the section of FIG. 7. Since the spot weld of the stick or cladding type has a nugget through thickness that is much less than that of the "Good" spot weld, the lower attenuation of the thinner nugget (compared to the good weld) results in a much lower signal to signal attenuation and often the top plate backwall echo is also evident, leading to intermediate peaks.

Thus the back wall signals are spaced at total weld thickness ($t_{64}+t_{62}+t_{66}$-indentation) with significant intermediate signals representing the back wall of the upper layer 64. +In one example, an automated decision maker computer system can display green for acceptable, red for reject and orange for further testing.

Figure 14:
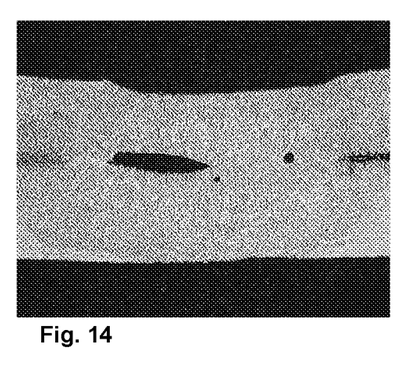
FIG. 14 is a cross-section through a weld with pores.
Figure 15:
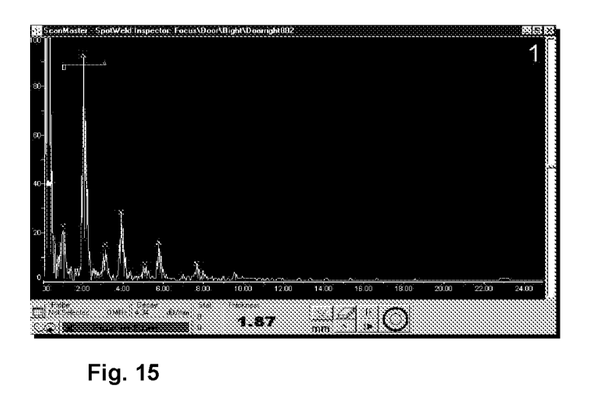
FIG. 15 is an A scan pattern of the weld with pores.

FIG. 14 is a cross-section through a weld 142 with pores 144, 146. With reference to FIG. 15, an A scan pattern for the weld 142 with pores 144, 146 of FIG. 14 is shown. The incident ultrasonic signal is partially reflected by the pores (flaws) in spot. The Intermediate echoes position indicates the depth of the pore (flaw).

A problem with the two dimensional image of a weld created by ultrasonic probing will have nugget borders indicated by a change in signal attenuation. The size of the nugget indicated may not correlate well to the actual quality of the nugget determined by destructive testing.

Instead of mechanically scanning a probe over the weld, good results may be obtained using a multiple detector array where the size of the array is large enough to cover the largest nugget. Where a 2 dimensional sensor array is used, a two dimensional image of the spot weld may be produced.

Embodiments of the invention use phased array (PA) probes. Instead of building a 2 dimensional map based on analyzing signal attenuation at each individual element or group of elements, it is possible to build a two dimensional may by analyzing the A-scan at each individual element or group of elements. Such sensor array probes show areas with good nugget, no nugget, voids, abutting but non-welded interface, etc. and thus the shape and size of the nugget can be determined, together with an indication of its quality. If, a color scheme is used, with, say, green for good, red for bad and orange for reconsideration, the number of green pixels in the two dimensional pixilated array gives an indication of quality for the weld as a whole.

Figure 16:
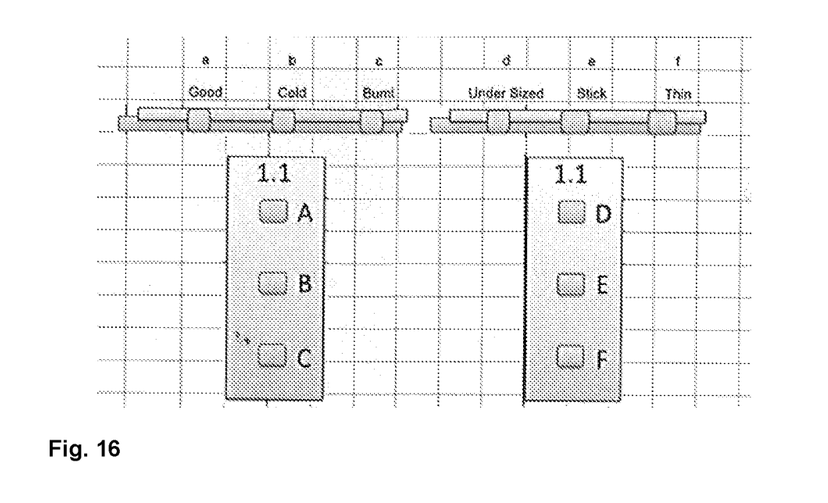
FIG. 16 is a schematic illustration of an array of weld spots.

A series of test coupons as shown in FIG. 16 was obtained and scanned using a sensor consisting of a two dimensional array of ultrasonic probes. For each sensor a phased array scan was performed.

The results of the ultrasonic testing for each sensor were considered good weld (green), no weld (blue), a thin weld where the actual thickness was less than the nominal thickness (orange), a discrepancy that was rejected is given in red, and where no measurement was possible, the signal is given in grey, as per table 1.

TABLE 1 showing how a pixel corresponding to a detected signal by a sensor in an array of sensors may be used to give an indication of local weld quality

| Element Color | On Screen Representation | UT (Decision) |
|---|---|---|
| Green | | Good |
| Blue | | Tl ToF (no weld) |
| Orange | | Actual TT < Nominal TT |
| Red | | Algorithm reject (discrepant) |
| Grey | | Measurement reject |

Figure 17:
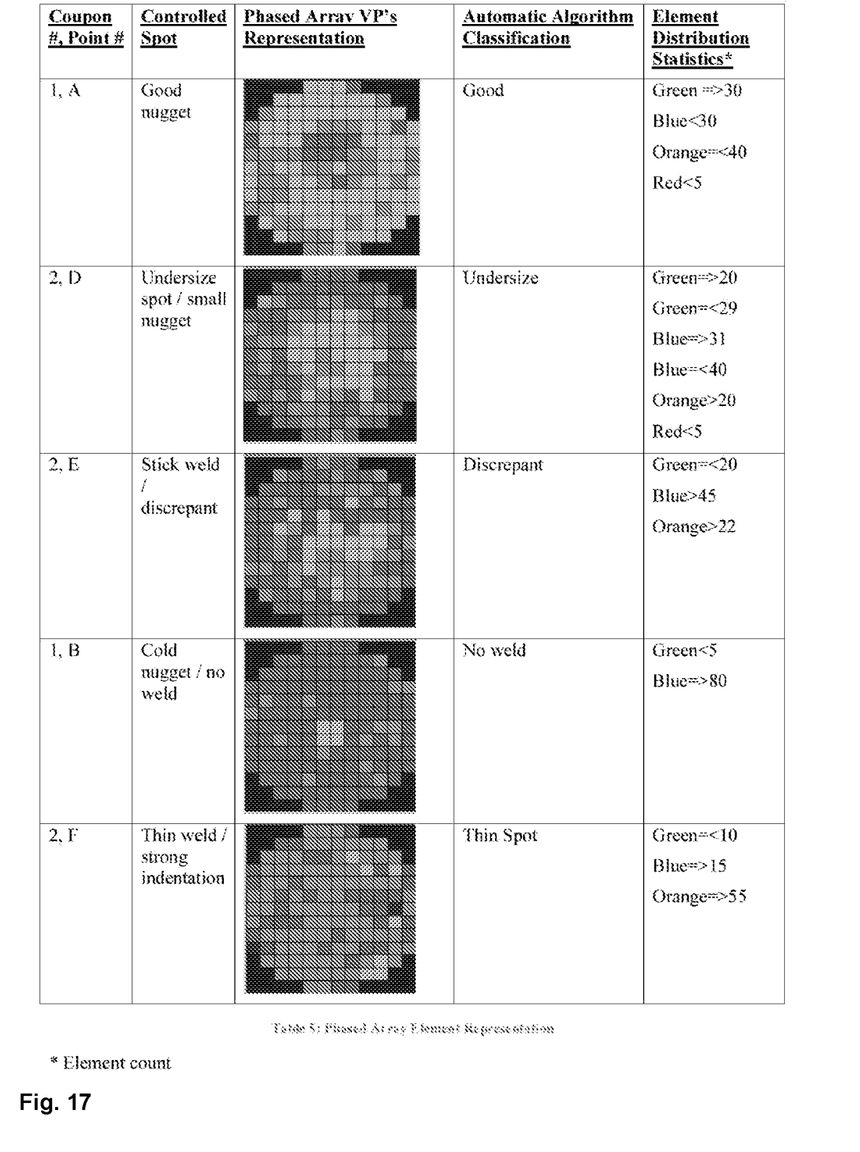
FIG. 17 is a pixilated color mapping of the world spots of FIG. 16, for characterization using tables 2 and 3.

The date generated by the multi-signal probe array is shown in FIG. 17. By setting appropriate thresholds, spot welds can be classifications. For example, with respect to table 2, a range of classifications based on the accumulated data is given.

TABLE 2 showing how a pixilated array corresponding to the detected signal by sensors in an array of sensors may be used to give a detailed indication of weld quality by setting appropriate thresholds.

| Decision | Condition |
|---|---|
| No Weld | # blue elements exceeding "no weld" TH |
| Good weld | # of green elements exceeding "good weld" TH |
| Undersized | # of green elements exceeding "undersize" TH AND lower than "good weld" TH |
| Discrepant | # of green elements lower than "undersize" TH |
| Thin spot | # of orange elements exceeding "thin spot" TH |

Thus, where, until now, a two dimensional array merely gave the overall size and shape of the nugget, this more detailed analysis gives an indication of quality, based on a calculation of the area with the pixels indicating good acoustic coupling, as well as enabling bad welds to be classified by a statistical method that sets acceptable threshold levels and automated decision making This can reduce wastage by avoiding scrapping of small but flawless nuggets, for example.

TABLE 3 corresponding to FIG. 16

| Coupon #, Point # | Controlled Spot |
|---|---|
| 1, A | Good nugget |
| 1, B | Cold nugget/no weld |
| 1, C | Burnt spot/over weld |
| 2, D | Undersize spot/small nugget |
| 2, E | Stick weld/discrepant |
| 2, F | Thin weld/strong indentation |

Persons skilled in the art will appreciate that the present invention is not limited to what has been particularly shown and described hereinabove. Rather the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A system for determining the quality of a spot weld in a workpiece, comprising:
   an ultrasonic probe comprising a two-dimensional array of ultrasonic sensors placed above a selected weld spot over a work surface;
   a display screen for displaying visual information related to ultrasound signal attenuation; and
   a computer configured to:
   receive from each sensor in the array a raw ultrasonic A-scan, wherein each A-scan includes a reflected ultrasonic wave from the single weld spot;
   identify intensity peaks, as function of distance, in each A-scan;
   analyze an intensity of each A-scan versus a distance inside the workpiece;
   for each A-scan detect if there are intermediate signals between the peaks;
   assign a color mark for each A-scan based on the analysis and the detection;
   generate a color map, comprising the color marks of each A-scan;
   count numbers of A-scans assigned with the same color mark, for all A-scans in the map; and
   determine a quality of the spot weld as a whole based on the numbers.

2. The system of claim 1, wherein each signal corresponds to a pixel in an array of pixels.

3. The system of claim 2, wherein each pixel in the array is assigned a color according to its weld quality level value.

4. The system of claim 1, wherein the weld quality is classified as good if no intermediate signal is detected.

5. The system of claim 1, wherein the weld quality is classified as one of: stick spot and clad spot, if intermediate signals between the peaks are detected.

6. The system of claim 1, wherein the computer is configured to determine the weld thickness based on the analysis of the intensity peaks.

* * * * *